United States Patent

McKinlay

Patent Number: 6,041,661
Date of Patent: *Mar. 28, 2000

[54] METHOD AND APPARATUS OF TESTING BOARD PRODUCT

[75] Inventor: Peter Robert McKinlay, Doncaster, Australia

[73] Assignee: AMCOR Limited, South Melbourne, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/930,938
[22] PCT Filed: Apr. 23, 1996
[86] PCT No.: PCT/AU96/00235
  § 371 Date: Nov. 12, 1997
  § 102(e) Date: Nov. 12, 1997
[87] PCT Pub. No.: WO96/34286
  PCT Pub. Date: Oct. 31, 1996

[30] Foreign Application Priority Data

Apr. 24, 1995 [AU] Australia .................. PN 2604

[51] Int. Cl.[7] ..................................... G01N 3/20
[52] U.S. Cl. .............................. 73/849; 73/851
[58] Field of Search .............. 73/826, 830, 831, 73/834, 849, 851, 853, 854

[56] References Cited

U.S. PATENT DOCUMENTS

| | | |
|---|---|---|
| 1,443,877 | 1/1923 | Guelbaum . |
| 2,426,583 | 9/1947 | Balley . |
| 2,693,107 | 11/1954 | Paden . |
| 3,158,021 | 11/1964 | Walters et al. . |
| 4,358,962 | 11/1982 | Ashby et al. ............... 73/849 |
| 4,687,106 | 8/1987 | Prins ............................. 73/849 |
| 5,503,024 | 4/1996 | Bechtel et al. ............. 73/849 |
| 5,574,227 | 11/1996 | Allan ............................. 73/849 |

FOREIGN PATENT DOCUMENTS

| | | |
|---|---|---|
| 57020/86 | 1/1986 | Australia . |
| 29703/89 | 8/1989 | Australia . |
| 1015222 | 12/1966 | United Kingdom . |
| 1145702 | 3/1969 | United Kingdom . |
| 1377607 | 12/1974 | United Kingdom . |

*Primary Examiner*—Max Noori
*Attorney, Agent, or Firm*—Alston & Bird LLP

[57] ABSTRACT

This invention relates to a method and apparatus for obtaining data relating to the compressive failure characteristics of a liner of a board sample which includes the following. A sample is aligned within a pivotal retaining mechanism of a testing device adapted to rotate about a line. A displacement force is applied at a constant rate to at least one edge of the liner such that the rotatable retaining mechanism allows self-positioning of the sample. Measurements are taken regularly of load and/or deflection observed until the liner fails.

10 Claims, 3 Drawing Sheets

SECTION POINT 2
IE 22        VALUE
-3.5 2E - 03
-7.8 6E - 03
-7.2 1E - 03
-6.5 5E - 03
-5.9 0E - 03
-5.2 4E - 03
-4.5 8E - 03
-3.9 9E - 03
-2.2 7E - 03
-1.9 6E - 03
-1.3 0E - 03
-6.5 2E - 04
+4.0 3E - 06

SECTION POINT 2
IE 22        VALUE
-1.1 3E - 03
-1.0 3E - 03
-9.9 1E - 03
-8.9 5E - 03
-7.9 9E - 03
-6.0 6E - 03
-5.1 0E - 03
-4.1 4E - 03
-3.1 8E - 03
-2.2 2E - 03
-1.2 6E - 03
-3.0 1E - 04
+6.5 9E - 06

METHOD AND APPARATUS OF TESTING BOARD PRODUCT

The invention relates to a method of testing paper board and cardboard products to measure and determine the integrity and quality of the paper board or cardboard product. In particular, the method of testing is directed to measuring and determining the compressive failure characteristics of corrugated board for use in box manufacture.

When corrugated board is used in box construction, the failure of the board will generally occur where the liner of the board structure is required to sustain the largest strains. A large displacement bending mode is observed, where the liner on the concave side is required to sustain the strains as previously mentioned. Generally, these compressive strains are accommodated by localised buckling of the liner between the flute tips of the corrugated board. The stress at which this happens depends upon the material used in constructing the board and the integrity with which the board has been formed and in particular, how the components have been glued together.

When strains become sufficiently large the liner becomes unstable, so that the energy stored in the board is dissipated in a very localised region involving the collapse of the liner material itself.

A number of attempts have been made to ascertain the integrity and quality of any particular board product to be used in box manufacture. One particular method is what is called the "Edge Crush Test" (ECT). There have been a number of methods developed to measure the edgewise compressive strength, but essentially what is common to all methods is that, a sample of board product is crushed. The difficulties with most of the ECT methods is that the edges always tend to fail first and whether the sample fails at the edges seems to be dependent upon whether or not the sample has been correctly cut. There are two major reasons why edge failure testing is not desirable. The first is that most corrugated board product when used in box manufacture does not fail at the edges. Secondly, there is a need to have a test which has easily reproducible results and is not dependent upon how accurately the sample is cut.

Some attempts have been made to address these problems of edgewise failure and ease of obtaining reproducible results using the conventional ECT, however, all of the methods to date have required either extremely complex machinery to prepare the uniquely shaped samples and equally complex machinery to perform the crushing action. In most instances the results have not been reliable or reproducible.

The other problem associated with existing edgewise crush strength tests is that both liner boards are compressed at the same level. In order to determine the compressive strength of the board product, prior art edge crush tests provide an averaged value from the inside and outside liner for the compressive strength of the sample. The average values obtained from prior art methods do not mirror accurately what happens during box failure where it is usually the inside liner, which is under the most strain, that fails.

Another method previously used to determine the integrity characteristics of a sample of board product is the pinch test. In this test the sample is gripped at either end and the ends are merely pushed together. As with the edge crush tests the problems associated with this method is that quite often there is failure at the edges as opposed to the centre of the sample. Furthermore, there are additional stresses introduced at the edges of the sample as a result of the clamping means, resulting in particularly unreliable indications of failure characteristics.

Thus there was, prior to the present invention, a need for a means of determining accurately and quantitatively the quality and strength characteristics of corrugated board for use in box manufacture, in order to predict its behaviour in use.

The present invention provides a method of characterising the compressive failure characteristics of board product including the steps of:

(a) aligning a liner face of a board sample within a testing means;

(b) applying a displacement at a constant rate to the edge of the liner face until the sample fails; and (c) regularly taking measurements of load and deflection observed.

It is preferred that the sample is aligned within two opposing retaining means. It is also preferred that the opposed retaining means each have a line about which they rotate, such that a line passing through the edges of the sample which are held in the retaining means is substantially parallel to and concurrent with the rotation line of the retaining means. It is further preferred that the rotation line is provided by a free moving hinge.

More preferably a rectangular sample is clamped within retaining means which are hinged about a line concurrent with a plane containing the end of the sample and a plane containing the external face of the liner to be tested such that the major portion of the sample is displaced to one side of said retaining means. This ensures a reasonably flat sample will buckle with the face to be tested under compression.

The invention also provides an apparatus for characterising the compressive failure characteristics of board product including:

(a) at least two retaining means for holding a test sample;

(b) a displacement applying means;

(c) means to measure a load exerted by the sample;

(d) means to measure the deflection of the sample under load.

It is preferred that the retaining means of the apparatus each have a line about which they rotate, such that a line passing through the edges of the sample which are held in the retaining means is substantially parallel to and concurrent with the rotation line of the retaining means.

It is also preferred that the sample is clamped within the retaining means which are hinged about a line concurrent with a plane containing the end of the sample and a plane containing the external face of the liner to be tested such that the major portion of the sample is displaced to one side of the retaining means.

The present invention is predicated upon the discovery that by aligning the sample of board product such that the liner face to be tested is aligned with the hinge line or pivot points of the means which restrains the sample, compressive strains can be introduced in the liner face under test without introducing high strains in the region of the restraining means.

Advantageously, the invention provides true values of compressive strength of the sample independent of any interference from edge conditions of the sample.

The invention will be better understood with reference to the accompanying drawings.

Figure 1:
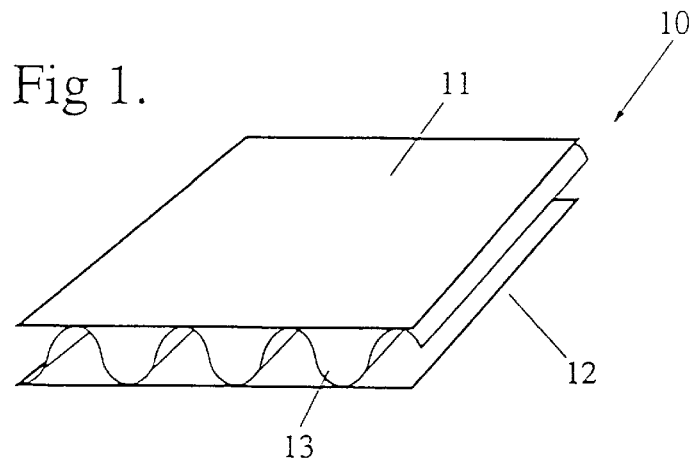
FIG. 1 illustrates a typical corrugated board structure.

FIG. 1 illustrates a typical corrugated board structure, 10, comprising two liners, 11 and 12, attached to the corrugated medium, 13. Of course, corrugated board product and board product to be used in box manufacture, can vary from the illustrated arrangement, by the number of liners used as well as the number of corrugated mediums. The combination of the liners and mediums in a typical board product can vary widely, depending upon the ultimate end use of the board. FIG. 1 is enclosed to illustrate the meanings of liners and corrugated mediums.

Figure 2:
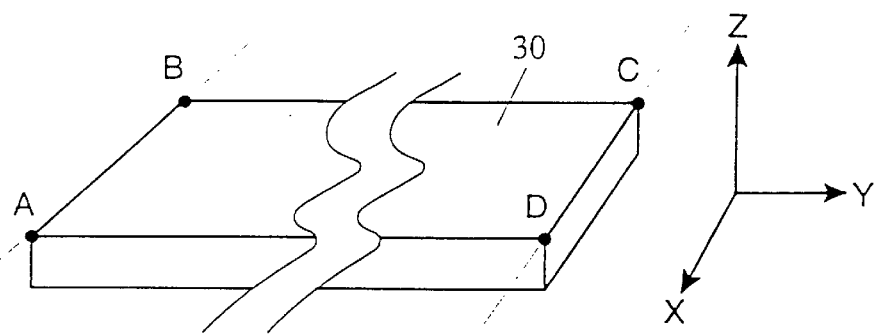
FIG. 2 illustrates a diagrammatic view of a board sample that can be used in the method of the present invention.
Figure 4:
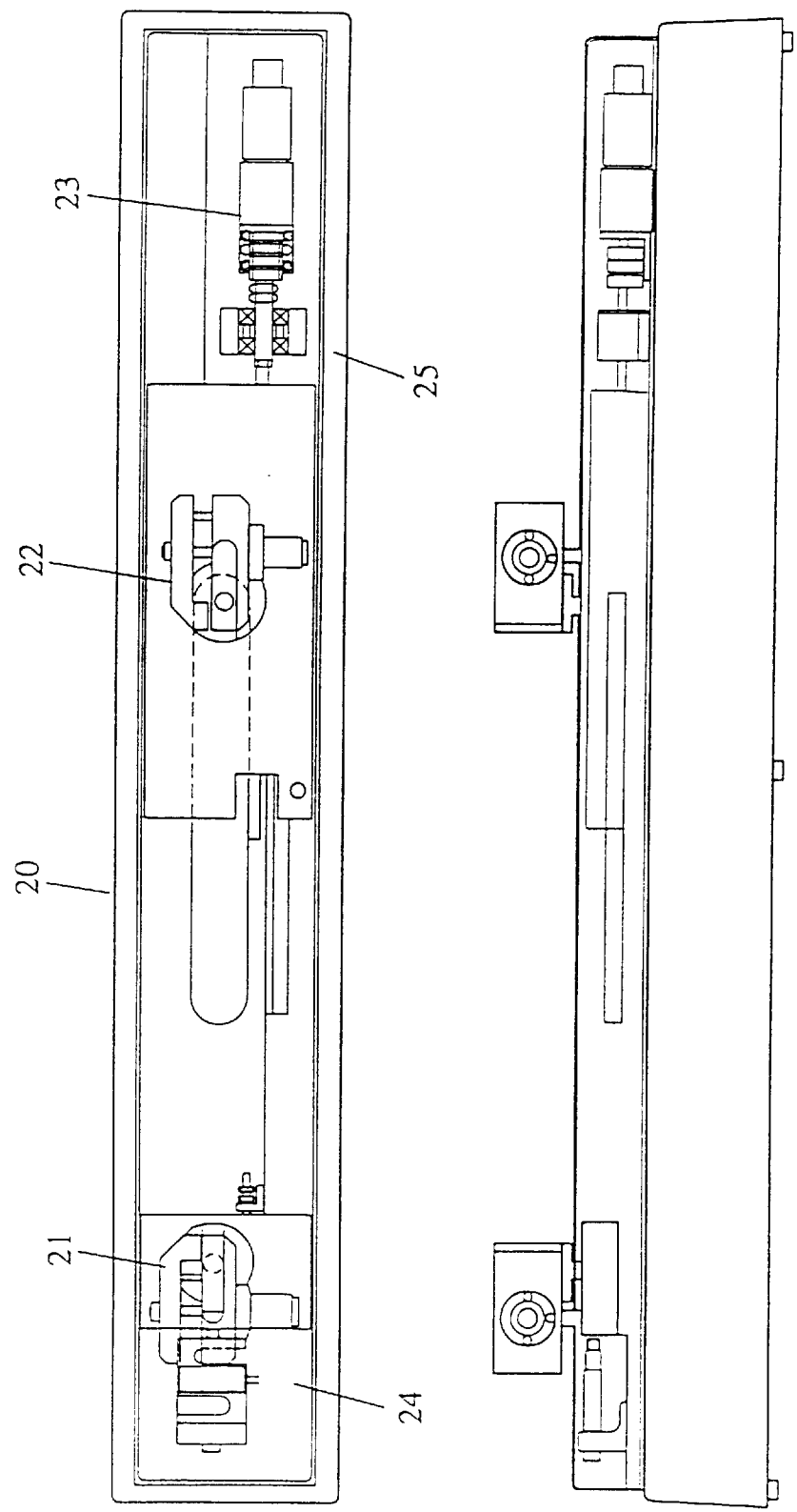
FIG. 4 illustrates the preferred apparatus of the present invention.

The method of the invention is conducted using a sample not dissimilar to the sample, 30, shown in FIG. 2. The sample, 30, with points ABCD is placed into an apparatus as illustrated in FIG. 4. The sample, 30, is set up vertically so that the point of failure can be visually observed.

The apparatus, as illustrated in FIG. 4 includes at least two retaining means for holding the test sample (21,22). These retaining means retain the sample by means of a hinged clip, the clip holding the sample, and the hinge being free moving in order to move with the sample during the test.

The retaining means (21,22) is attached to a load measuring means (24) and a displacement effecting means (23) below the hinged clips.

Typically a sample, 30, of board, generally with dimensions 100 mm wide and 500 mm long is held along its short edges (AB and CD of the sample, 30, —see FIG. 2) via retaining means 21 and 22. The retaining means, 21 and 22, are each hinged about a line which when the sample, 30, is held within the retaining means, 21 and 22, the hinge line is parallel to lines AB and CD of sample, 30. Additionally, the hinge lines of retaining means, 21 and 22, lie in the plane containing the external face of the liner to be tested, which results in a portion of displaced material to one side of the hinge. In particular the inside liner (of a box) is the one that generally fails and as such is the one normally tested. The sample under test is clamped through a motor driven ballscrew assembly retaining means (21,22). The torque of the DC motor can be controlled and therefore control the sample clamping pressure.

In the testing routine, the sample under test is not held tightly until a sharp rise in load occurs, signalling the sample is completely in the retaining means and load is applied directly on the end of the sample. Once this occurs, the retaining means are clamped to an appropriate pressure.

In operation, the sample, 30, is placed in the retaining means and the test is commenced, such that the lines AB and CD move toward each other in the Y-direction as illustrated in FIG. 2. The lines AB and CD of the sample, 30, move toward each other at a specified rate causing the sample 30, to buckle in the Z-direction, resulting in the test face ABCD being compressed. The hinges of the retaining means are free to move with the sample as it changes shape during the test.

The applied displacement generates a load on the sample from a moving retaining means (22) to the stationary retaining means (21). The stationary retaining means (21) is attached to a load measuring device (24) of 450N full scale (0.1% linearity). The moving retaining means is driven from a ball screw through a DC motor and gear box (23). The speed of the motor can be controlled. Measurement of speed is enabled through an optical encoder directly mounted on the motor shaft (25).

The electrical signal from the load measuring device is conditioned and measurement of the analogue signal directly represents the load. Deflection (or retaining means travel) is derived from knowing the gearbox reduction ratio, the ball screw pitch and the number of revolutions taken from the optical encoder (25).

Displacement applying means, 23, of the apparatus can be any conventional displacement means, such as a motor driven screw, hydraulic actuator, rack and pinion, solenoid actuator; however, the preferred displacing means is by a motor driven precision screw.

The load exerted upon the retaining means, 21 and 22, by the board product sample, 30, is measured and plotted against the displacement of the ends of the sample, 30, in the Y-direction. A typical graph obtained from the method of the present invention is illustrated in FIG. 3.

Figure 3:
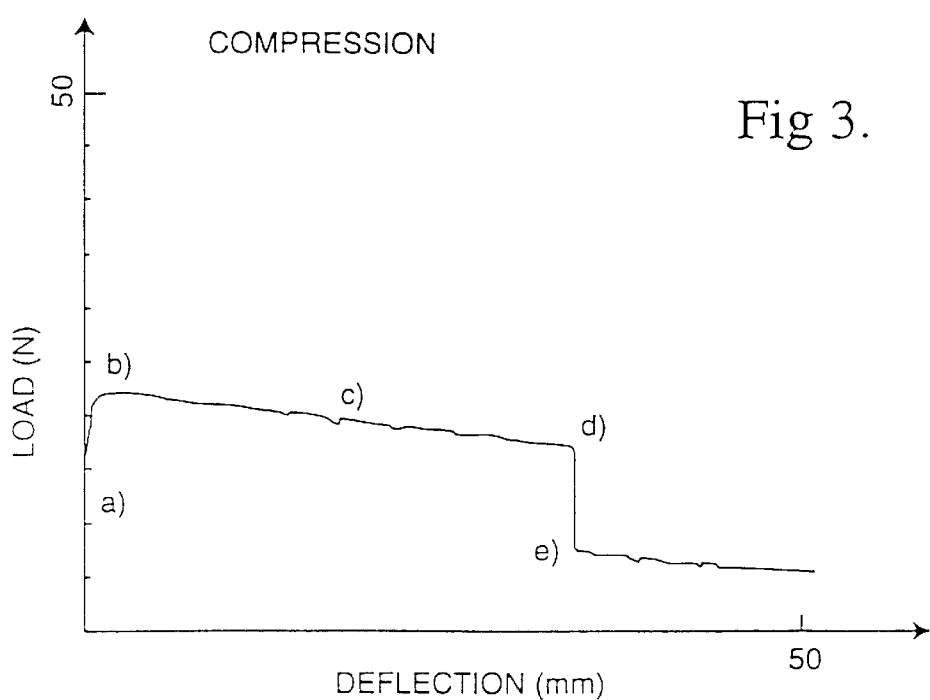
FIG. 3 illustrates a typical Load v Deflection plot obtained from the method of the present invention.

With reference to FIG. 3, the graph exhibits five features of the product:

(a) Initial Stiffness of the sample—this is related to the elastic properties of the component materials from which the board is made and the sample dimensions;

(b) Buckling Load—the load at which the sample buckles and is related to the elastic properties of the sample and sample dimensions;

(c) Post Buckling Slope—provides details of the elastic and inelastic stability of the liner under test;

(d) Liner failure point—at this point the sample energy becomes localised within the liner and supporting medium. The load suddenly drops at this point. A shift in the liner failure point either to the left or right gives an indication of the structural integrity of the board product. For example a premature failure point indicates a loss of structural integrity, perhaps caused by lack of glue coverage or wash boarding;

(e) Post failure load—this provides a quantitative value of the strength of the structure after the localised failure.

As a general observation of the Load v Deflection curve, it is noted that if the curve per se is translated in either an upwards or downwards direction, there is a change in the characteristics of the paper. If there is a translation of the curve in the sideways direction, either left or right, there is a change in the characteristics of the structure of the board.

Figure 5:
FIG. 5 illustrates the vertical component of the inelastic strain in the concave (test) liner of a sample just prior to failure.
Figure 5:
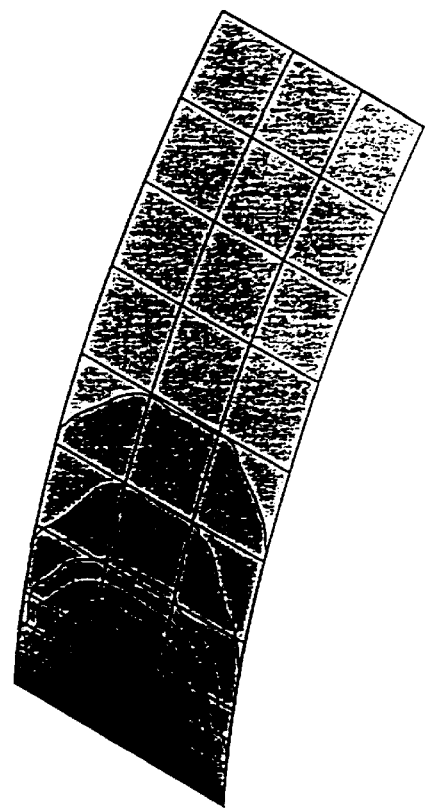
Figure 6:
FIG. 6 illustrates the inelastic strain in the sample after failure.
Figure 6:
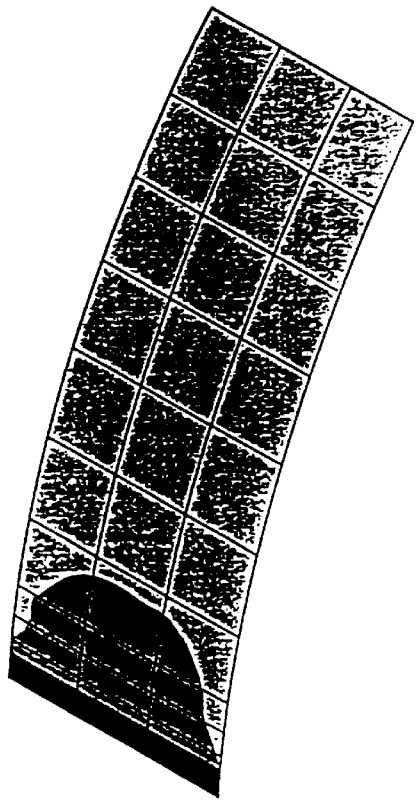

As indicated previously the present invention is predicated on the ability to measure the true failure characteristics of a particular sample independent of any interference from edge failure. Reference is made to FIG. 5 which illustrates the vertical component of the inelastic (non recoverable) strain occurring in the concave liner, just before the strain becomes localised and fails. It is noted that the largest strain occurs in the body of the material and not at the free edges. Thus when localisation (failure of the liner) occurs, it takes place well removed from any free edge and thus the results obtained represent the true intrinsic failure level of the sample independent of the edge conditions. After localisation (failure of the liner) occurs, all of the inelastic strain is concentrated along the failure line at the centre of the sample as illustrated in FIG. 6. This failure line corresponds on the crease line observed on the actual sample.

The process and apparatus of the present invention are applicable for use in both the machine (MD) and cross machine (CD) directions of the board sample. The process of the invention may also be conducted at a series of angles to create a polar diagram of pertinent sample characteristics, such as failure strain or post buckling slope.

It is envisaged that the procedure will be used in the production of boxes and trays etc., after each step to monitor the quality of the product. Defects in the manufacture of board product, whereby the components lose structural integrity from lack of adequate glue coverage or from washboarding will be identified by the method of the present invention. It is proposed that the process and apparatus of the present invention will be used in combination with the AMCOR MD shear test and also the AMCOR glue bond integrity test, to provide a comprehensive measure of board and in particular corrugate board quality.

Thus the present invention provides a definitive method and apparatus for characterising the compressive failure characteristics of corrugated board in a manner which is relevant to predicting end use applications such as box compression strength and tray bulge.

I claim:

1. A method of obtaining data relating to the compressive failure characteristics of a liner of a board sample, including the steps of:
   (a) aligning the sample within retaining means of a testing device, the retaining means adapted to rotate freely about a line such that the retaining means moves with the sample during a test;
   (b) applying a displacement force at a constant rate to at least one edge of the liner along a direction from said at least one edge toward an opposite edge of the sample so as to place the liner in compression, such that the rotatable retaining means moves with the sample as the sample changes shape as a result of the applied force; and
   (c) regularly taking measurements of at least one of a load and a deflection of the sample until the liner fails.

2. The method of claim 1 wherein the sample is placed within two opposing retaining means, and one retaining means is rotatable while the other is stationary.

3. A method as claimed in claim 1 wherein the board sample is aligned in the retaining means such that a line which passes through an edge of the liner held in the retaining means is substantially parallel to and concurrent with the line about which the retaining means rotates.

4. A method as claimed in claim 1 wherein the line about which the retaining means rotates, lies in a plane containing an external face of the liner to be tested, such that, during testing, a portion of the sample is displaced to one side of the retaining means.

5. A method as claimed in claim 1 wherein an internal liner of the sample is displaced to one side of the retaining means during testing.

6. An apparatus for obtaining data relating to the compressive failure characteristics of a liner of a board sample including:
   (a) retaining means in which the sample being tested is aligned, the retaining means being rotatable about a line such that the retaining means moves with the sample during a test;
   (b) means for applying a displacement force at a constant rate to at least one edge of the liner along a direction from said at least one edge toward an opposite edge of the sample so as to place the liner in compression; and
   (c) means to measure at least one of the load exerted on the sample and the deflection of the sample under load.

7. The apparatus of claim 6 wherein the retaining means comprises two opposing clamping means, and one clamping means is rotatable while the other is stationary.

8. The apparatus as claimed in claim 6 wherein a line which passes through an edge of the liner held in the retaining means is substantially parallel to and concurrent with the line about which the retaining means is rotatable.

9. An apparatus as claimed in claim 6 wherein the line about which the retaining means rotates lies in a plane containing an external face of the liner to be tested which results in a portion of the sample being displaced to one side of the retaining means, when in use.

10. The apparatus of claim 6 wherein the rotatable retaining means is provided by a free moving hinge.

* * * * *